(12) United States Patent
Jackson

(10) Patent No.: US 8,163,568 B2
(45) Date of Patent: Apr. 24, 2012

(54) RECORDING ASSAY DEVICE

(75) Inventor: James Richard Jackson, Abingdon (GB)

(73) Assignee: Smart Sensor Telemed Ltd., Oxfordshire (GB)

( * ) Notice: Subject to any disclaimer, the term of this patent is extended or adjusted under 35 U.S.C. 154(b) by 0 days.

(21) Appl. No.: 13/113,477

(22) Filed: May 23, 2011

(65) Prior Publication Data

US 2011/0236914 A1    Sep. 29, 2011

Related U.S. Application Data

(60) Division of application No. 12/069,915, filed on Feb. 13, 2008, now Pat. No. 7,947,490, which is a continuation of application No. 09/381,561, filed as application No. PCT/GB98/00815 on Mar. 18, 1998, now abandoned.

(30) Foreign Application Priority Data

Mar. 19, 1997 (GB) .................................. 9705667.5

(51) Int. Cl.
*G01N 33/543* (2006.01)
(52) U.S. Cl. ........................................ 436/518; 436/807
(58) Field of Classification Search .................. None
See application file for complete search history.

(56) References Cited

U.S. PATENT DOCUMENTS

| | | | |
|---|---|---|---|
| 4,756,884 A | 7/1988 | Hillman et al. | |
| 4,803,170 A | 2/1989 | Stanton et al. | |
| 4,963,498 A | 10/1990 | Hillman et al. | |
| 5,179,005 A | 1/1993 | Phillips et al. | |
| 5,182,191 A | 1/1993 | Fan et al. | |
| 5,426,032 A | 6/1995 | Phillips et al. | |
| 5,637,469 A | 6/1997 | Wilding et al. | |
| 5,695,623 A | 12/1997 | Michel et al. | |
| 5,695,949 A | 12/1997 | Galen et al. | |
| 5,726,026 A | 3/1998 | Wilding et al. | |
| 5,837,546 A | 11/1998 | Allen et al. | |
| 5,955,028 A | 9/1999 | Chow | |
| 6,014,438 A | 1/2000 | Quattrocchi | |
| 6,027,689 A | 2/2000 | Markart | |
| 7,947,490 B2 | 5/2011 | Jackson | |

FOREIGN PATENT DOCUMENTS

| | | |
|---|---|---|
| EP | 0885591 | 12/1998 |
| WO | 95/06240 | 3/1995 |

OTHER PUBLICATIONS

BIO-RAD catalogue: Think Twice.
Pharmacia Biotech Catalogue: Purification Systems and Media Selection Guide.

*Primary Examiner* — Chris L Chin
(74) *Attorney, Agent, or Firm* — Standley Law Group LLP

(57) ABSTRACT

A method for assaying a sample involves an assessment device having an assay part and a detachable recording part, which are disposed on separable portions of a substrate. The sample to be assayed is received in a sample application well on the assay element, where it contacts a measuring element, generally after being mixed with an assay reagent. Assay information relating to the sample is transferred from the measuring element to data recording element on the recording part. After the information transfer, the assay part and the recording are separated, so that the assay part can no longer transfer information to the data recording element.

12 Claims, 2 Drawing Sheets

RECORDING ASSAY DEVICE

CROSS-REFERENCE TO RELATED APPLICATIONS

This application is a division of, and is entitled to benefit of a right of priority under 35 USC §120 from U.S. Ser. No. 12/069,915, filed 13 Feb. 2008, now U.S. Pat. No. 7,947,490, which is a continuation of Ser. No. 09/381,561, filed 17 Sep. 1999, now abandoned, which is a 371 of international PCT/GB98/00815, filed 18 Mar. 1998, which claims priority to GB 9705667.5, filed 19 Mar. 1997, all of which are incorporated by reference as if fully recited herein.

TECHNICAL FIELD

The invention herein described is an assay and recording means for use in, particularly but not exclusively, the diagnosis and/or analysis of tissue and/or fluid samples taken from a human or animal which comprises an assay part and a detachable data recording part.

BACKGROUND

The analysis of tissue or fluid samples is of crucial importance if the appropriate diagnosis of a patient is to be made by a healthcare worker. Also, there are numerous conditions that need constant monitoring to maintain the correct treatment regime. For example, and not by way of limitation, infectious disease (including HIV), diabetes, osteoporosis, tumor cell markers, reproductive endocrinology, thyroid disease haematology, therapeutic drugs, drugs of abuse, cardiac disease, treatment monitoring clinical trials assessment.

Also, it is apparent that the human genome project will identify genes that are involved, either directly or indirectly, in a number of inherited genetic diseases. Clearly it will be important to efficiently process this genetic information to offer appropriate treatment and/or counseling to individuals that are genetically predisposed to certain diseases. It is highly likely that both conventional processing facilities (i.e., to deal with monitoring various metabolites as described above) and also new means to efficiently process genetic information will be required to deal with expanding healthcare.

It is also apparent that there are situations where adequate medical advice/treatment is either unavailable or not easily accessible to individuals. For example, and not by way of limitation, armed forces personnel on active service in war zones, armed forces personnel on active service in non-war situations but are effectively remote from medical assistance (i.e., ships, submarines, etc.), individuals that farm in remote areas (i.e., Australian Outback, Africa), individuals who work for long periods away from adequate medical assistance (i.e., workers on oil/gas installations, research workers in polar or tropical regions, merchant navy personnel). It is important that these individuals receive rapid and reliable diagnosis of their condition so that the correct treatment is administered.

Also a number of the planet's inhabitants live on remote islands that do not have extensive medical support and may require a rapid means to diagnose a condition that obviates the need for the individual to visit a mainland hospital or alternatively for a doctor to visit the individual on the island to remove samples for analysis.

On a less extreme note there are examples where, although a hospital is local to an individual, there may be extenuating circumstances that prevent or make difficult the attendance of the individual at an outpatient's clinic to give samples for testing. Those suffering, for example, from bronchitis or emphysema, the elderly and infirm and any other individuals who would find a trip to their local hospital physically stressful and potentially hazardous. Currently, patients of this type can have home visits to monitor their condition. However, these are expensive and time consuming since some of a healthcare worker's effective time is spent travelling to the patient's home.

In addition it may be desirable to analyze the recorded result of an assay by a healthcare worker at a data processing site remote from the patient rather than rely on the patient to record and report the result of the test. There are certain patients (i.e., those suffering from mental disorders, e.g., depression, schizophrenia), where it may be desirable to keep the results of an assay secret until the healthcare worker can process the data to enable the correct diagnosis to be determined. It is well known in the art that patients can willfully interfere with an assay to give an erroneous measure of the particular variable monitored by the assay. If the recording device merely records the information for subsequent processing and analysis this possibility is minimized.

This has particular relevance in clinical trial assessment of candidate drugs to provide a non-biased data collection means from treated and placebo groups to ensure a reliable assessment of drug efficacy is obtained. It is therefore an object of the invention to provide a generic assay and a recording device which efficiently monitors an individual's health status. It is a further object of the invention to provide an assay and recording means wherein said recording means is detachable from said assay means.

SUMMARY

According to a first aspect of the invention there is provided an assessment device comprising an assay part and a recording part wherein said recording part is detachable from said assay part.

In a preferred embodiment of the invention said assessment device is selectively sized and shaped to facilitate handling and transport of the assessment device to the relevant processing facility.

In a preferred embodiment of the invention said recording device is selectively sized and shaped to facilitate handling and transport of the recording device to the relevant processing facility.

The above embodiment relates to a recording device that is sufficiently small and light to be transported via a conventional transport means for example, and not by way of limitation, the postal service or courier service.

In an alternative preferred embodiment of the invention said recording device may be adapted to facilitate data transfer via electronic means. It will be apparent that in subsequent years the use of the Internet will become more widely accessible to the general public. The recording device may, therefore, be adapted to interface with a personal computer within an individual's home or place of work. Data transfer ideally will be encrypted to prevent third party access and decoded at a processing facility via a responsible healthcare worker.

In yet a further preferred embodiment of the invention said detachable recording device is provided in retro-fit form, i.e., it may be desirable to adapt a pre-existing assay device to receive a recording part to enable data recording and storage.

It will be apparent from the above embodiment that the assessment device may be manufactured as a single unit. Alternatively, via suitable adaptation, said recording part or device may be attached to an existing assay part or device to enable data recording.

In yet a further preferred embodiment said recording device is a micro processor or other similar electronic device. Alternatively, said recording device is photographic, comprising, for example, a photographic emulsion, the stored images of which are developed at a processing facility.

It will be apparent that the above means for recording data from the assay can be processed by conventional means at the processing facility by down loading the stored information/images at a computer by a healthcare worker. Alternatively, if the worker has access to the Internet the data/images can be transferred electronically from the individual to the healthcare worker at the processing facility.

In yet a further preferred embodiment of the invention there is provided an assessment device comprising an assay part with at least one sample application well.

Reference herein to sample application well is intended to encompass any receptacle, recess, indentation, or well into which a tissue/fluid sample can be placed.

Reference herein to a fluid sample is intended to include both a liquid and a gas sample, for example, urine, blood, saliva, mucous, pus, semen, breath.

In a preferred embodiment of the invention said recording assay device is characterized by multiple sample application wells. Ideally, one or more of said well or wells are provided, suitably impregnated, with materials for sampling said fluid sample.

In yet a further preferred embodiment of the invention said assay part is adapted by the provision of at least one primary conduit in fluid connection with said sample application well. Ideally said primary conduit contains assay reagents in some instances suitable for diluting said sample fluid. More preferably further still, said conduit is suitably sized to facilitate capillary flow of said sample fluid therethrough.

In yet a further preferred embodiment of the invention said assay part is further adapted by the provision of at least one secondary conduit which is in fluid connection with one or more of said sample application wells; and which is ideally also adapted to provide for capillary flow therethrough. Preferably further still said secondary conduit contains assay reagents, ideally of a nature different to the assay reagents in said primary conduit but most suitably compatible therewith so as to provide, in total, for the complete and selected assaying of said fluid sample as it flows through either or both of said primary/secondary conduits.

In yet a further preferred embodiment of the invention at least one control or calibration is provided in the assessing device. For example, a control conduit may be provided for monitoring flow through the device. Said control conduit may optionally be provided with assay reagents, or alternatively, the elements, to be detected by the assay in order to produce a positive result or identification.

In yet still a further preferred embodiment of the invention there is provided an assay part provided with at least one assay conduit which is further characterized by a detection zone to facilitate the detection of the product(s) of the assay.

According to yet a further aspect of the invention there is provided a method to assay and record a tissue/fluid sample from an individual comprising:

(i) applying a sample to a sample application well of an assessment device as herein described;

(ii) mixing said sample with at least primary assay reagents; and (iii) recording the data from i-ii via the recording part.

It will be apparent to one skilled in the art that this method enables the rapid processing of an applied fluid/tissue sample within minutes of application to the sample well. This will reduce erroneous assay of samples due to sample degradation during long term storage.

It is well known in the art that assay reagents comprise, and not by way of limitation, buffers, substrates, enzymes, antibodies, co-factors, intermediary metabolites, nucleic acid. It will also be apparent that there are well known in the art means to assay various factors. For example, antibody techniques using polyclonal/monoclonal antibodies to specific epitopes (e.g., drugs, hormones, steroids, tumor specific cell surface antigens, viral/bacterial antigens). Enzyme based techniques for monitoring, for example, glucose or cholesterol in blood plasma. Many of these techniques rely on a color change as an indication of the presence of the desired agent(s). More recently chemiluminescent and/or fluorescent detection means are available and will be applicable to the assay recording device.

According to yet a further aspect of the invention there is provided a kit comprising; an assessment device as herein described, assay reagents and optionally protective packaging for transport of the recording device to the processing facility.

It will be apparent that the recording assay device has widespread application in the diagnosis of disease. It may also have a role in clinical trials assessment of potential therapeutic agents providing a non-biased means of collecting data from treated and placebo groups to ensure a reliable assessment of drug efficacy is obtained.

BRIEF DESCRIPTION OF THE DRAWINGS

An embodiment of the invention will now be described, by example only, and with reference to the following figures wherein.

DETAILED DESCRIPTION

Figure 1:
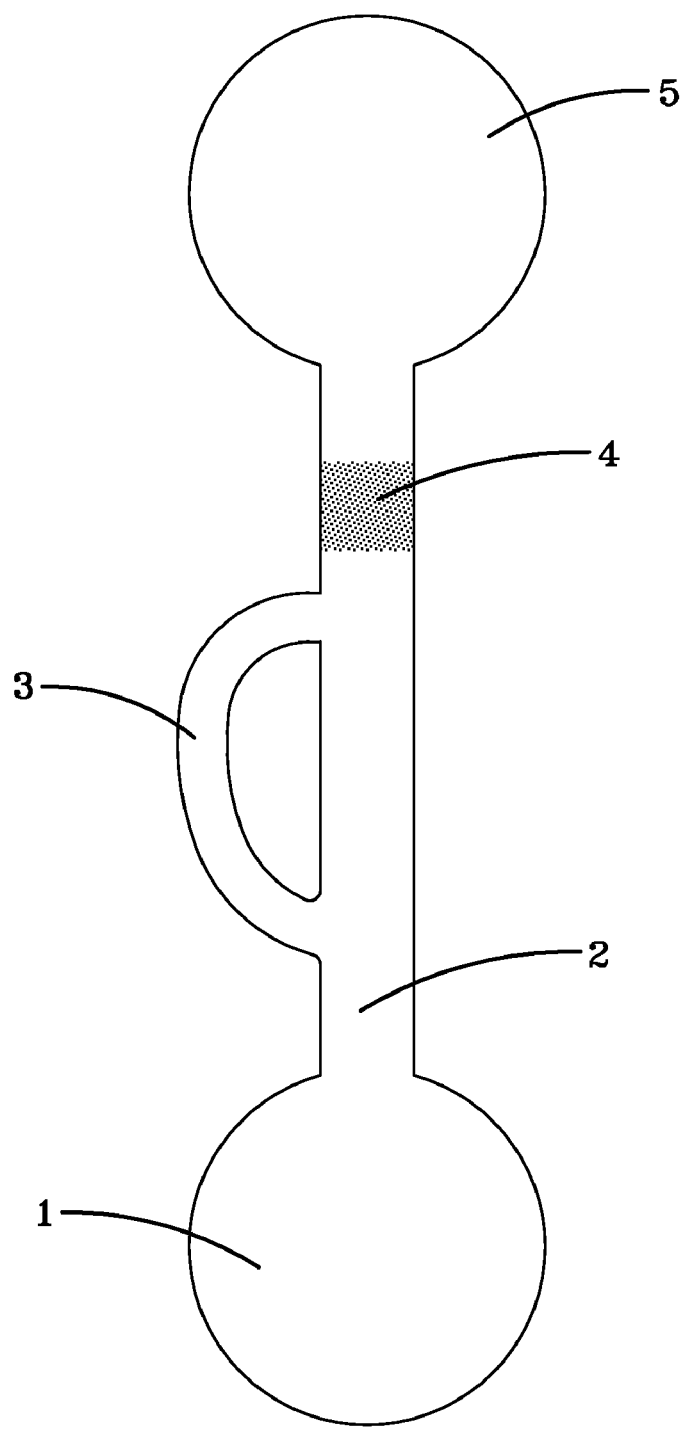
FIG. 1 is a diagrammatic representation of the assay part of an assessment device.

Referring to FIG. 1, a diagrammatic representation of an assay part of the recording assay device is shown. The assay part is characterized by the presence of a selectively sized and shaped sample application well (1) which is circular in the diagram. The sample application well (1) is in fluid contact with a primary assay reagent conduit (2). The primary reagent conduit is selectively sized to facilitate the movement of sample applied to the application well (1) by capillary flow. The primary reagent conduit contains at least some of the reagents necessary to complete a reaction with the sample applied to the sample well (1) or begin an initial reaction with the applied sample. Additionally the reagents may represent solutions used to dilute the sample and/or primary assay reagents. A single assay well (1) is shown in the diagram. However, the device may be adapted to contain multiple application wells in fluid contact with one or more primary reagent conduits.

The primary assay reagent conduit comprises filter paper, or other suitable means, impregnated with the primary assay reagents and can comprise additionally, or alternatively, any of the following alternatives;

(i) multiple channels formed in paper or other water permeable material by impregnation with polymers to form water impermeable regions;

(ii) multiple channels formed in nitrocellulose or other water permeable diagnostic or filter membrane by impregnation with wax to form water impermeable regions;

(iii) formation of strips of water permeable material within a sheet of the material by cutting regions from a sheet of the material, in order to form multiple channels;

(iv) printing (e.g., by silk screen) of a water permeable material (e.g., nitrocellulose or other material used to make diagnostic and filter membranes) In emulsion or other fluid form onto a water impermeable surface to create channels of the water permeable material;

(v) multiple water permeable channels comprised of any material and produced by any method;

(vi) a single water permeable channel or strip comprised of any material and produced by any method. In a single channel device there would be one or more detection zones;

(vii) a channel(s) of free space, within a water impermeable structure, forming a capillary in which liquid may flow by capillary action. This technique is sometimes referred to as a "capillary flow" diagnostic device. In a single channel device there would be one or more detection zones; and (viii) other types of channel.

In use a fresh sample applied at (1) is moved via capillary action into the primary reagent conduit. The filter paper may be hydrophilic over at least part of its area to restrict and/or concentrate the flow of sample along the primary conduit (2).

The primary reagent conduit is optionally in fluid contact with a secondary reagent conduit (3) containing secondary assay reagents. The secondary reagent conduit is selectively sized to facilitate capillary flow of sample from the primary reagent conduit. FIG. 1 represents a single secondary reagent conduit. In an alternative embodiment of the invention more than one secondary reagent conduit may be present containing reagents required to complete the assay. Again capillary flow will draw the sample/primary assay reagent mix into the secondary assay conduit (3) to facilitate the reaction of secondary reagents with the sample/primary assay reagent mix. A detection zone (4) is selectively positioned to interact with the reaction mixture once all components have been mixed and the assay completed. The detection zone (4) may contain substrates necessary to allow detection of the product of the assay. Alternatively, these substrates may be incorporated in the primary and/or secondary mix. Detection may be via a color change or other suitable means (e.g., chemiluminescence; fluorescence emission). Two preferred detection means are readily applicable to the assessment device:

(i) recording of an electrochemical reaction by a microprocessor or other solid-state device. Amperometric and potentiometric assay detection techniques are appropriate. This is the preferred detection system, as the removable recording system can be kept from contacting physically with any of the components of the sample by means of the electrical connection between the detection zone and the recording device, thus rendering it completely safe from infectious risk on handling; and (ii) recording of a photometric reaction by a photographic or other light sensitive film or device.

Chemiluminescence and fluorescence are appropriate. The film and detection zone can be separated by a clear water impermeable layer which will prevent the film from contacting physically with any of the components of the sample.

Additionally other detection means include;

(iii) reflectance or transmittance photometry; production of a stable dye on a surface by biochemical or chemical reaction, including ELISA;

(iv) microparticles, including polymers, metallic and non-metallic elements and other materials;

(v) soluble colored substances, including dyes. These would be determined by a light reflectance technique (including fluorimetry) or light transmittance technique or another technique related to any specific feature of any soluble substance used; and (vi) other assay detection systems.

Figure 2:
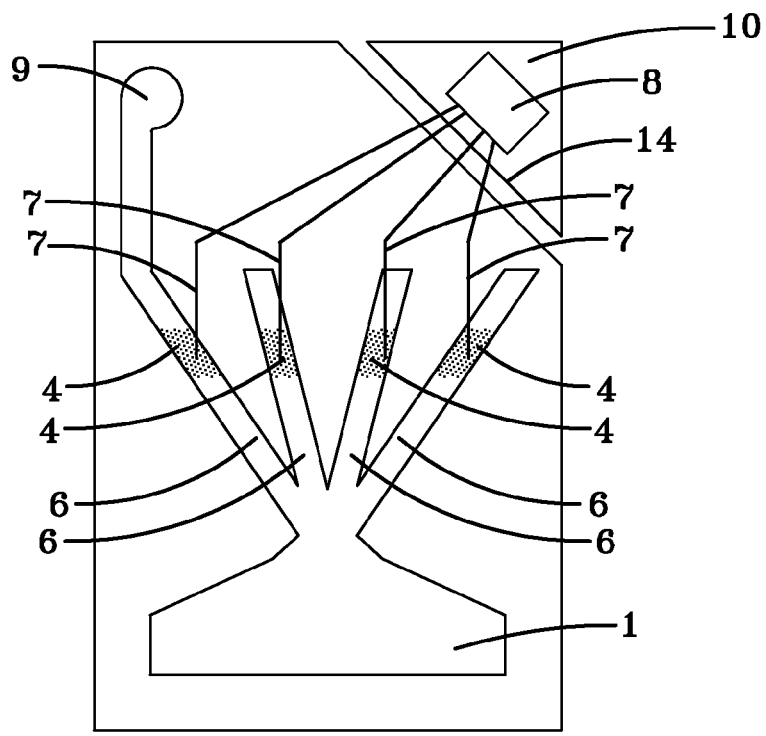
FIG. 2 is a diagrammatic representation of the internal layout of an assessment device.

The detection is recorded and stored in a microprocessor located in the recording means, not shown in FIG. 1. The assay part is further adapted by the provision of a waste well (5) to store excess sample/reaction mix. Referring to FIG. 2, an alternative embodiment of an assay part is shown diagrammatically with a detachable recording part (7). The single sample application well is shown (1) in fluid connection with a plurality of conduits (6). The conduits identified in FIG. 2 may contain alternate assay reagents to facilitate multiple testing of variables of the applied sample. For instance, glucose, salts, hormone levels, the detection of specific epitopes via immune reaction. The plurality of conduits (6) each contain a detection zone (4), each of which is connected to a microprocessor (8) via electrical connections (7) to facilitate interrogation of the assay in the detection zone (4). The assay recording device is also provided with a test ready indicator (9) to monitor device status thereby allowing the user to readily identify when the device has completed the assay.

Figure 3:
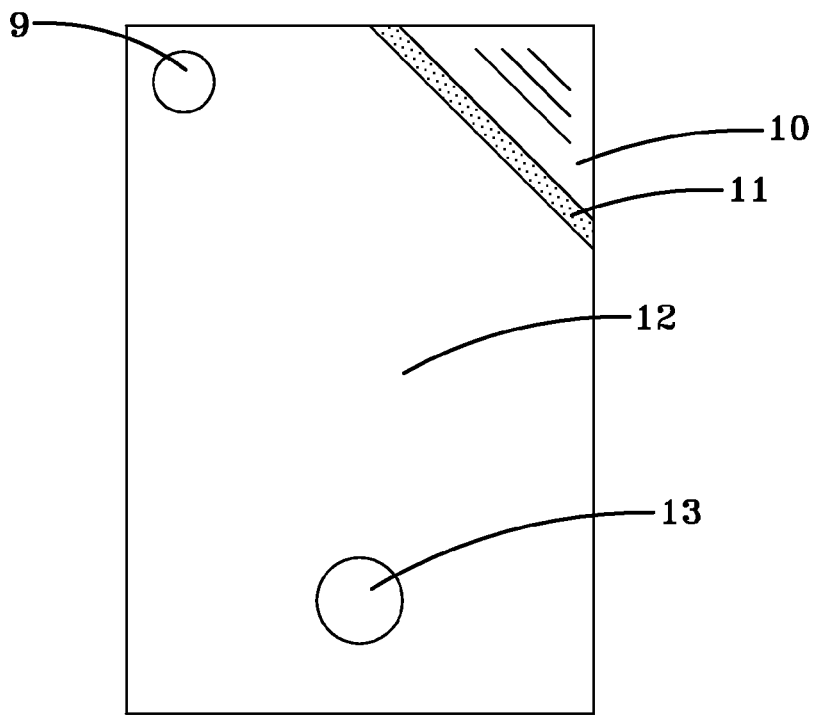
FIG. 3 represents a diagrammatic representation of an external view of an assessment device.

Referring to FIG. 3, an external diagrammatic representation of an assay/recording device is shown. The outer casing (12) is manufactured from a durable material, (e.g., reinforced plastic). The recording part is easily detached from the assay part via a perforated attachment means (11). Alternatively the assay part and recording part may be selectively attached via a clip, hasp, lock, or any suitable means to facilitate the attachment or detachment of said assay part from said recording part. In use the patient applies a sample to a sample well (1) through an application port (13). When sufficient time has lapsed to allow the assay to reach an end point the test ready indicator (9) conveys this to the user. The user can then simply detach the recording part from the assay part and send the data to a processing facility for decoding and interrogation.

The invention, therefore, provides for a device that operates in a stable, reliable and reproducible manner and advantageously the results of the assay are not available to a user until further remote, processing has occurred.

What is claimed is:

1. A method for assaying a sample, comprising the steps of:
providing an assessment device having an assay element and a data recording element arranged on a substrate and connected by way of a communication conduit;
receiving a sample within a sample application well on the assay element;
mixing the sample with an assay reagent;
detecting assay information relating to the sample;
transmitting, by way of the communication conduit, the assay information from the assay element to the data recording element;
recording the assay information within the data recording element; and
separating, irreversibly, the communication conduit after the recording step.

2. The method of claim 1, wherein:
the separating step is accomplished by breaking the substrate irreversibly into first and second portions, with the assay element on the first portion and the data recording element on the second portion.

3. The method of claim 2, further comprising the step of:
providing an actuating signal to an indicator upon completion of the recording step.

4. The method of claim 1, further comprising the step of:
providing an actuating signal to an indicator upon completion of the recording step.

5. The method of claim 1, further comprising the step of:
downloading the assay information electronically from the data recording element to a processing facility after the separating step.

6. The method of claim 2, further comprising the step of:
downloading the assay information electronically from the data recording element to a processing facility after the separating step.

7. The method of claim 3, further comprising the step of:
downloading the assay information electronically from the data recording element to a processing facility after the separating step.

8. The method of claim 4, further comprising the step of:
downloading the assay information electronically from the data recording element to a processing facility after the separating step.

9. The method of claim 1, wherein:
the separating step is accomplished by:
inserting the assessment device in a casing; and
breaking the substrate of the assessment device irreversibly into first and second portions, with the assay element on the first portion and the data recording element on the second portion, using a separation line defined by the casing.

10. The method of claim 9, further comprising the step of:
providing an actuating signal to an indicator upon completion of the recording step.

11. The method of claim 10, further comprising the step of:
downloading the assay information electronically from the data recording element to a processing facility after the separating step.

12. The method of claim 9, further comprising the step of:
downloading the assay information electronically from the data recording element to a processing facility after the separating step.

\* \* \* \* \*